United States Patent
Laruelle et al.

(10) Patent No.: US 11,433,348 B2
(45) Date of Patent: Sep. 6, 2022

(54) METHOD AND APPARATUS FOR RECYCLING HEPTAFLUOROISOBUTYRONITRILE

(71) Applicant: GENERAL ELECTRIC TECHNOLOGY GMBH, Baden (CH)

(72) Inventors: Elodie Laruelle, Le Peage-de-Roussillon (FR); Louis Maksoud, Villeurbanne (FR); Yannick Kieffel, Saint-Jean-de-Bournay (FR)

(73) Assignee: General Electric Technology GmbH, Baden (CH)

( * ) Notice: Subject to any disclaimer, the term of this patent is extended or adjusted under 35 U.S.C. 154(b) by 0 days.

(21) Appl. No.: 17/036,846

(22) Filed: Sep. 29, 2020

(65) Prior Publication Data
US 2021/0093995 A1   Apr. 1, 2021

(30) Foreign Application Priority Data

Sep. 30, 2019   (EP) .................................. 19290099

(51) Int. Cl.
*B01D 53/22*   (2006.01)
*B01D 71/48*   (2006.01)
(Continued)

(52) U.S. Cl.
CPC ......... *B01D 53/229* (2013.01); *B01D 53/228* (2013.01); *B01D 71/48* (2013.01);
(Continued)

(58) Field of Classification Search
CPC ...... B01D 71/50; B01D 71/48; B01D 53/229; B01D 2311/2626; B01D 2253/104;
(Continued)

(56) References Cited

U.S. PATENT DOCUMENTS

| 5,730,779 A | 3/1998 | Chernyakov et al. |
| 5,919,285 A | 7/1999 | Li et al. |

(Continued)

FOREIGN PATENT DOCUMENTS

| EP | 1 184 068 A1 | 3/2002 |
| WO | 2016/128571 A1 | 8/2016 |

(Continued)

OTHER PUBLICATIONS

Freeman et al., "Hybrid membrane-absorption CO2 capture process," ScienceDirect, https://www.sciencedirect.com/science/article/pii/S1876610214018803?via%3Dihub, 9 pages.

(Continued)

*Primary Examiner* — Anthony R Shumate
(74) *Attorney, Agent, or Firm* — Eversheds Sutherland (US) LLP

(57) ABSTRACT

A method and device for purifying heptafluoroisobutyronitrile and a dilution gas from a used gas mixture comprising heptafluoroisobutyronitrile, a dilution gas and arcing byproducts. The method comprising the steps of (a) contacting the used gas mixture with at least one adsorbent material to generate a gas stream depleted in arcing by-products;

(b) contacting the gas stream depleted in by-products with a first membrane to obtain a first permeate stream rich in the dilution gas, and a first retentate stream rich in heptafluoroisobutyronitrile;

(Continued)

(c) contacting the first permeate stream rich in the dilution gas with a second membrane to obtain a second permeate stream rich in the dilution gas and a second retentate stream rich in heptafluoroisobutyronitrile; and (d) combining the first and second retentate streams rich in heptafluoroisobutyronitrile.

13 Claims, 3 Drawing Sheets

(51) Int. Cl.
| | | |
|---|---|---|
| *B01D 71/50* | (2006.01) | |
| *B01D 71/56* | (2006.01) | |
| *B01D 71/64* | (2006.01) | |
| *B01D 71/68* | (2006.01) | |
| *C07C 253/34* | (2006.01) | |
| *C07C 255/10* | (2006.01) | |

(52) U.S. Cl.
CPC .............. *B01D 71/50* (2013.01); *B01D 71/56* (2013.01); *B01D 71/64* (2013.01); *B01D 71/68* (2013.01); *C07C 253/34* (2013.01); *B01D 2253/104* (2013.01); *B01D 2311/2626* (2013.01); *C07C 255/10* (2013.01)

(58) Field of Classification Search
CPC ...... B01D 53/228; B01D 71/64; B01D 71/68; B01D 71/56; C07C 255/10; C07C 253/34
See application file for complete search history.

(56) References Cited

U.S. PATENT DOCUMENTS

| | | | |
|---|---|---|---|
| 2004/0045432 A1 | 3/2004 | Yamamoto | |
| 2010/0174047 A1* | 7/2010 | Jung | B01J 31/2239 |
| | | | 528/395 |
| 2015/0228375 A1* | 8/2015 | Kieffel | H02B 13/055 |
| | | | 361/604 |
| 2018/0296966 A1* | 10/2018 | Coignet | B01J 20/262 |

FOREIGN PATENT DOCUMENTS

| | | |
|---|---|---|
| WO | 2018/210936 A1 | 11/2018 |
| WO | 2018/210938 A1 | 11/2018 |

OTHER PUBLICATIONS

Extended Search Report issued in European Applicatin No. 19290099.1, dated Jan. 24, 2020, 8 pages.

European Search Report for Application No. 19290099.1 dated Jan. 16, 2020.

* cited by examiner

METHOD AND APPARATUS FOR RECYCLING HEPTAFLUOROISOBUTYRONITRILE

CROSS-REFERENCE TO RELATED APPLICATIONS

This application claims priority to European Application No. 19290099.1, filed Sep. 30, 2019, the contents of which are incorporated by reference.

BACKGROUND OF THE INVENTION $SF_6$ gas has been used since the 1970's in medium- and high-voltage equipment for insulation and arc extinguishing. For economical and environmental reasons, $SF_6$ manufacturers have developed technologies for $SF_6$ recycling in a closed loop.

However, alternative $SF_6$-free insulating gas mixtures with lower global warming potential have been introduced for use in medium- and high-voltage equipment. Such alternatives include gas mixtures comprising heptafluoroisobutyronitrile along with a dilution gas. However, the recycling and reuse of these insulation gases is challenging as such alternative gas mixtures comprise multiple components. Furthermore, the technology used for the purification and recycling of $SF_6$ is not applicable to $SF_6$ alternative gas mixtures given the differences in the composition of the by-products of arcing.

There is therefore a need for methods and apparatus for the recycling of $SF_6$ alternative gas mixtures, and in particular for the recycling of gas mixtures comprising heptafluoroisobutyronitrile.

SUMMARY OF THE INVENTION

The present invention is defined in the accompanying claims.

In one aspect, the present invention provides an apparatus for purifying heptafluoroisobutyronitrile and a dilution gas from a used gas mixture comprising heptafluoroisobutyronitrile, a dilution gas and arcing by-products, said apparatus comprising at least one adsorbent unit configured to remove a first group of arcing by-products from the used gas mixture, yielding a stream depleted from by-products;
a first membrane separation unit configured to separate the used gas mixture depleted from arcing by-products into a first permeate stream and a first retentate stream, wherein said first membrane separation unit comprises a first membrane unit feed inlet, a first membrane unit permeate gas outlet and a first membrane unit retentate gas outlet, wherein said first membrane unit feed inlet is downstream from the at least one adsorbent unit;
a second membrane separation unit configured to separate the first permeate stream into a dilution gas mixture and by-products, wherein said second membrane separation unit comprises a second membrane unit feed inlet, a second membrane unit permeate gas outlet and a second membrane unit retentate gas outlet, wherein the second membrane unit feed inlet is downstream from the first membrane unit permeate gas outlet.

In a second aspect, the present invention provides a method of purifying heptafluoroisobutyronitrile and a dilution gas from a used gas mixture comprising heptafluoroisobutyronitrile, a dilution gas and arcing by-products, said method comprising the steps of (a) contacting the used gas mixture with at least one adsorbent material to generate a gas stream depleted in arcing by-products;
(b) contacting the gas stream depleted in by-products with a first membrane to obtain a first permeate stream rich in the dilution gas, and a first retentate stream rich in heptafluoroisobutyronitrile;
(c) contacting the first permeate stream rich in the dilution gas with a second membrane to obtain a second permeate stream rich in the dilution gas and a second retentate stream rich in heptafluoroisobutyronitrile; and
(d) combining the first and second retentate streams rich in heptafluoroisobutyronitrile.

BRIEF DESCRIPTION OF THE DRAWINGS

The invention may be put into practice in various ways and a number of specific embodiments will be described by way of example to illustrate the invention with reference to the accompanying figures, in which.

DETAILED DESCRIPTION

Figure 1:
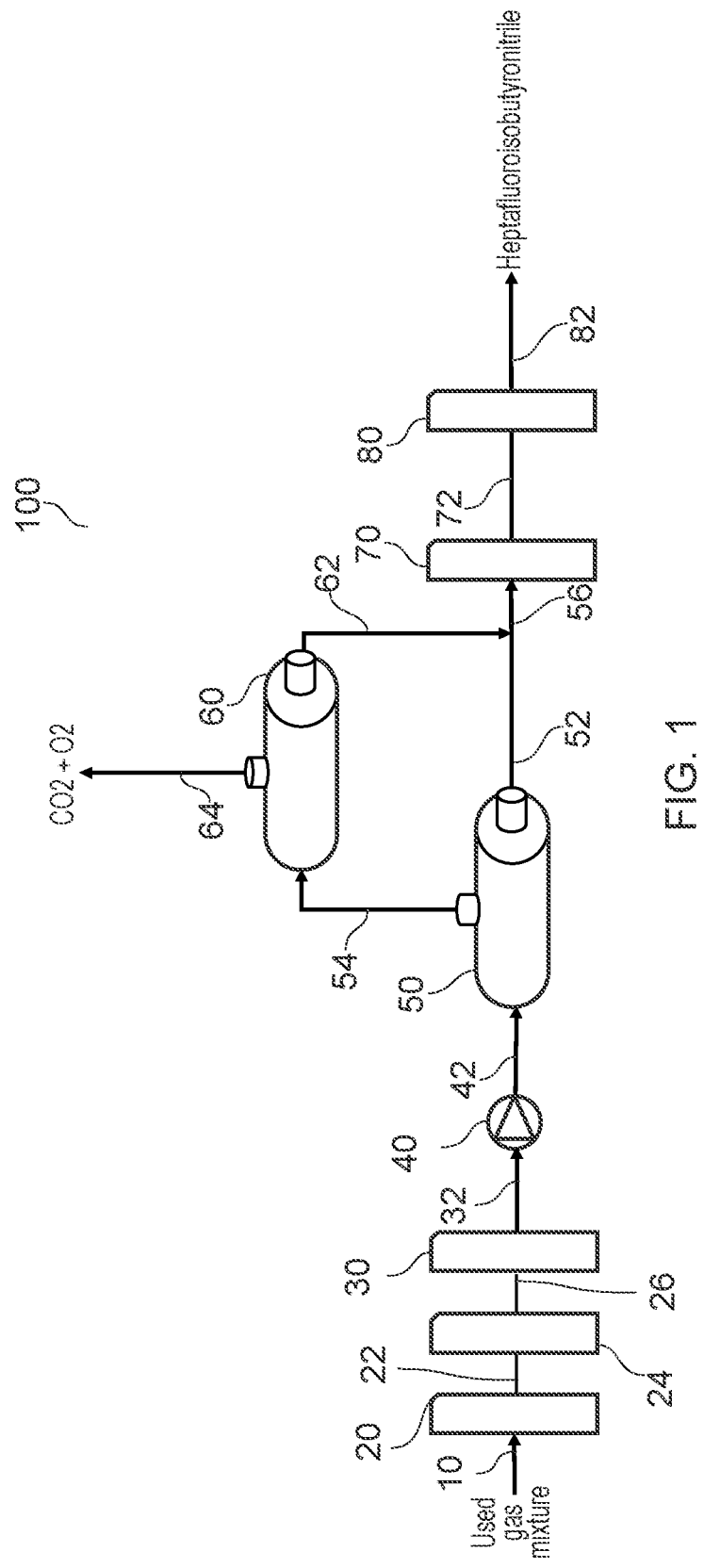
FIG. 1 is a scheme showing an embodiment of an apparatus according to the invention.

The meaning of terms used herein are explained below, and the present invention will be described in detail.

As used herein, the term "medium voltage" and "high voltage" are used in the conventionally accepted manner. In other words, the term "medium voltage" refers to a voltage that is greater than 1000 volts (V) for AC and 1500 V for DC, but that does not exceed 52000 V for AC or 75000 V for DC. The term "high voltage" refers to a voltage that is strictly greater than 52000 V for AC and 75000 V for DC.

As used herein, the term "comprises" means "includes, but is not limited to" any specified constituent component, process step or the like. The term "comprises" encompasses, without limitation, instances which "consists essentially of" any specified constituent component, process step or the like.

As used herein, the term "depleted" means that the concentration of a specified component(s) in the effluent stream in a particular separation step or unit is less than the concentration of the same component(s) in the feed stream to that particular separation step or unit.

As used herein, the term "rich" means that a concentration of a specified component(s) in the effluent stream of a particular separation step or unit is greater than the concentration of the same component(s) in the feed stream to that particular separation step or unit.

The terms gas, insulating gas, gas mixture and gas insulating mixture may be used herein interchangeably.

The gas mixture or gas insulation is a gas mixture including heptafluoroisobutyronitrile.

Heptafluoroisobutyronitrile, also known herein as $iC_3F_7CN$, has a formula (I) of $(CF_3)_2CFCN$ and corresponds to 2,3,3,3-tetrafluoro-2-trifluoromethyl propanenitrile, having CAS number 42532-60-5. It has a boiling point of −3.9° C. at 1013 hPa (boiling point measured in accordance with ASTM D1120-94 "Standard Test Method for Boiling Point of Engine Coolants").

As used herein, the term "used gas mixture" refers to a gas mixture which has been used in a medium-high-voltage electrical apparatus.

The used gas mixture comprises heptafluoroisobutyronitrile and a dilution gas. The amount of heptafluoroisobutyronitrile, in molar percentage, in a used gas mixture may be less than about 15%, less than about 10%, less than about 9%, less than about 8%, less than about 7%, less than about 6%, less than about 5%, less than about 4%, less than about 3%. Preferably, there is between 3 and 10% molar percent of heptafluoroisobutyronitrile.

A dilution gas is a neutral gas having a GWP that is very low, or even zero. The dilution gas may be carbon dioxide, having a GWP that is equal to 1, nitrogen, oxygen, or air, advantageously dry air, having a GWP that is equal to 0, or mixtures thereof. A dilution gas may be selected from the list consisting of carbon dioxide, nitrogen, oxygen, air (80% $N_2$ and 20% $O_2$), advantageously dry air (80% $N_2$ and 20% $O_2$, with less than 0.01% water), and any mixture thereof. Advantageously, heptafluoroisobutyronitrile may be used in a mixture with carbon dioxide and oxygen. The dilution gas may comprise at least 80% by volume, at least 90% by volume of carbon dioxide. The dilution gas may comprise 80-96% by volume of carbon dioxide and 1-10% by volume of oxygen.

As used herein, the term "by-product", or decomposition products, means compounds which are the result of the decomposition of any one of the components of an insulating gas mixture. Under medium- and high-voltage conditions, the components of the insulating gas decompose. For example, decomposition by-products of insulating compositions comprising heptafluoroisobutyronitrile and a dilution gas may contain components such as HF, CO, perfluoroacrylonitrile ($CF_2$=CFCN), ethandinitride (CN—CN), pentafluoroproprionitrile ($CF_3$—$CF_2$—CN), trifluoroacetonitrile ($CF_3$—CN), carbonyl fluoride and octafluoropropane ($COF_2$+$C_3F_8$), hexafluoroisobutyronitrile (($CF_3$)$_2$CHCN) and perfluoroisobutene (($CF_3$)$_2$C=$CF_2$).

The gas mixture is used to insulate and extinguish arcs in medium- and high-voltage electrical equipment. During use, if there is arc extinguishing, the gas mixture will decompose into several different components including CO and carbon-based compound by-products, such as various fluorocarbon-based by-products. The composition of the insulating gas mixture may therefore vary over time, depending on the level of arcing that occurs, and therefore have different amounts of (arcing) by-product which are generated. To maintain optimal insulating and arcing properties of the gas mixture, it may be necessary to change the gas mixture. As the concentration of heptafluoroisobutyronitrile is low in the gas mixture, and it is the most valuable component in the mixture, it would therefore be advantageous to have a method which purifies and enriches the amount of heptafluoroisobutyronitrile in a gas mixture for reuse. It would also be advantageous if the heptafluoroisobutyronitrile purification method would allow the release of dilution gases, free of by-products.

The apparatus of the present invention provides a series of units which enable the purification and enrichment of the used gas mixture to increase the amount of heptafluoroisobutyronitrile and purify the dilution gas.

Figure 2:
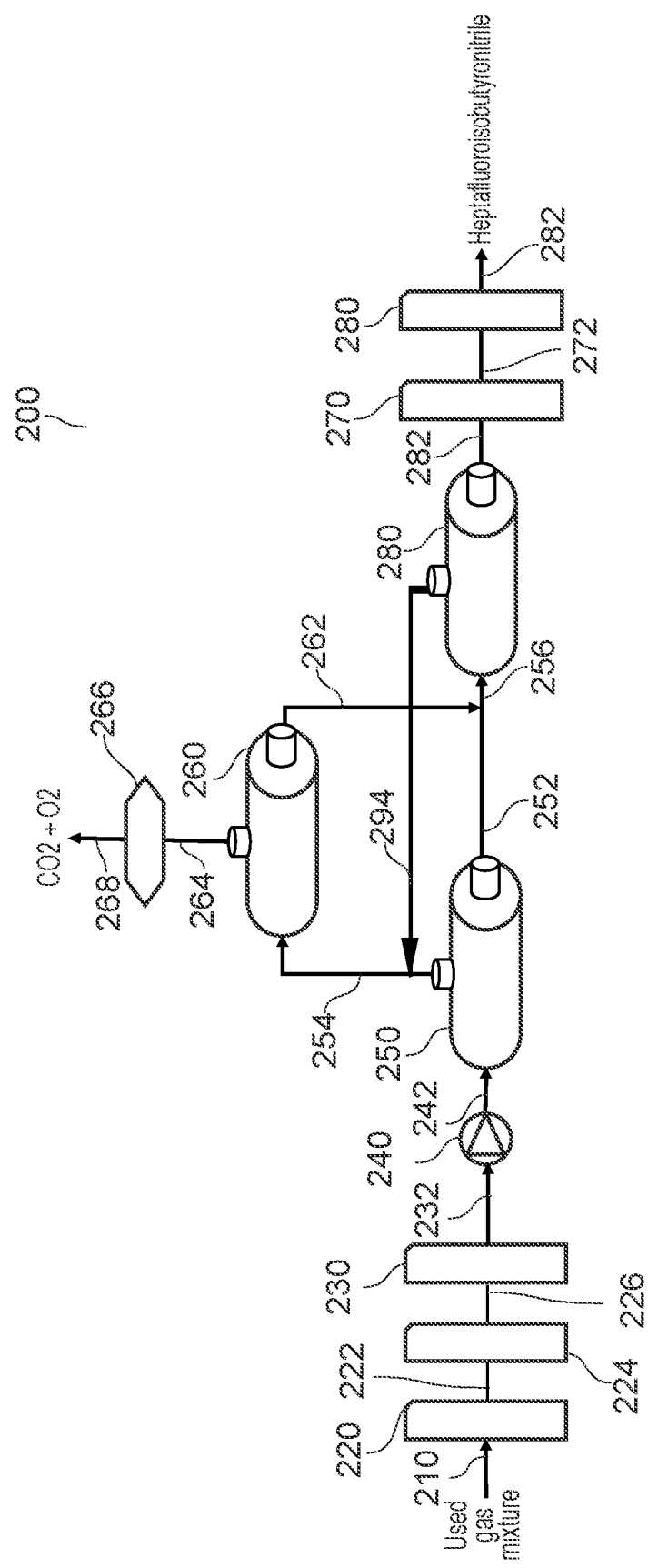
FIG. 2 shows a scheme showing a further embodiment of an apparatus according to the invention.
Figure 3:
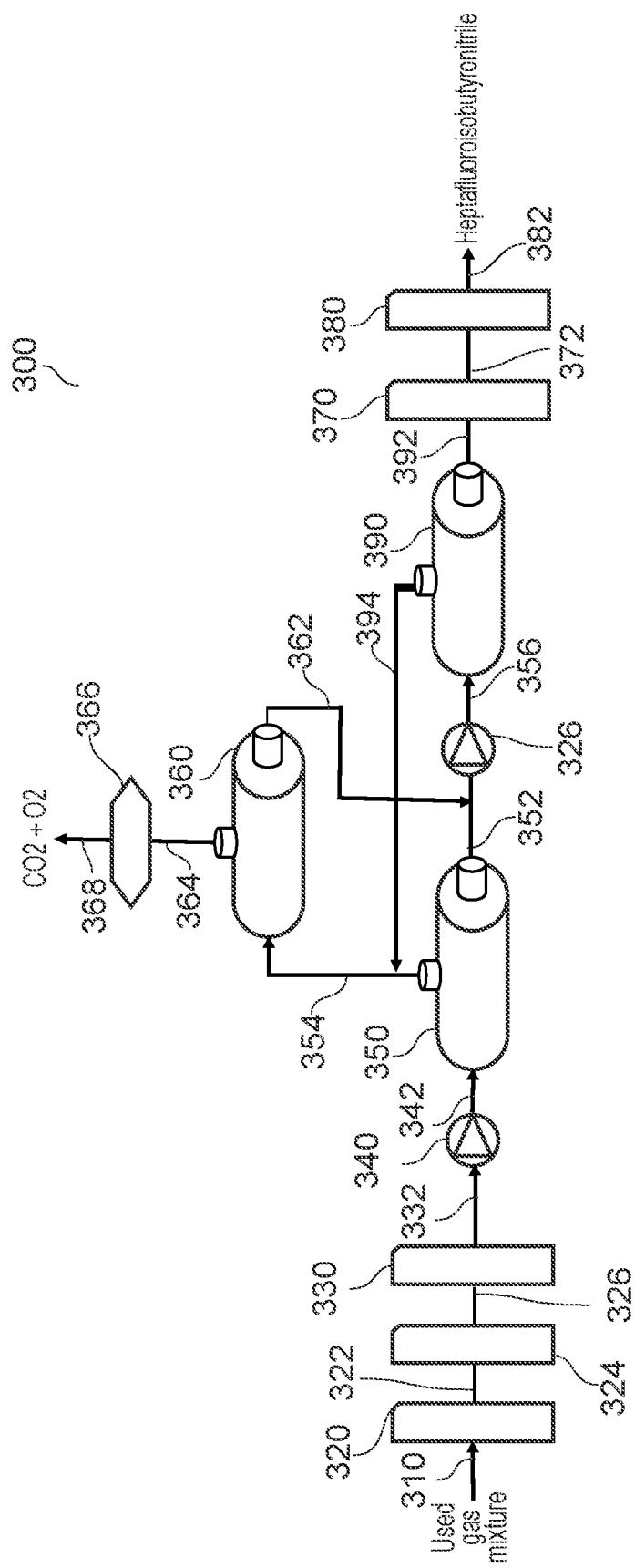
FIG. 3 shows a scheme showing a further embodiment of an apparatus according to the invention.

As can be seen from FIGS. 1, 2 and 3, the used insulating gas mixture 10, 210, 310 may be introduced into a conduit leading to a cotton-based particulate filter 20, 220, 320. The particulate filter 20, 220, 320 removes particulate matter, such as carbon particles, from the gas stream.

The gas stream depleted of particulate matter 22 may then be fed into a scrubber (absorbent) unit 24, 224, 324 for drying and removal of humidity. The material for scrubber unit 24, 224, 324 may be zeolite 3A.

Following drying, the gas stream 26, 226, 326 is fed into a filter (or scrubber) unit 30, 230, 330 also called by-product a by-product trap unit, for removing decomposition by-products of the arcing process. The material in the filter unit is suitable for removing decomposition by-products from the used gas mixture. Suitable materials include molecular sieves, soda lime, and activated alumina. Preferably, the material is a zeolite, more preferably zeolite 5A. The filter unit 30, 230, 330 may be configured to remove most of the by-products of arcing reactions, namely the carbon-based compounds or otherwise called here a first group of by-products.

The by-product trap filter 30, 230, 330 may be used at a pressure ranging from about 300 kPa to about 1000 kPa. The by-product filtration step may take place from about 20° C. to about 100° C.

The gas stream depleted of particulate matter and by-products 32, 232, 332 may then be regulated by subjecting it to a gas pressure regulating unit 40, 240, 340 to form a gas mixture with controlled pressure 42, 242, 342. The gas pressure regulating unit may compress the gas stream 32, 232, 332 if it is at low pressure. Alternatively, gas pressure regulating unit 40, 240, 340 may be a pressure reducer if the gas stream is at high pressure. The gas mixture 42, 242, 342 may have a pressure ranging from about 300 kPa to about 1000 kPa. Preferably, the gas pressure regulating unit 40, 240, 340 is sealed and oil-free.

The recycling system may comprise more than one gas pressure regulating unit. The gas pressure regulating units may be set up at various locations in the system. For example, as illustrated in FIG. 1, the gas pressure regulating unit is located downstream from the particulate filter 20. Alternatively, a further gas pressure regulating unit may be set up in the system of FIG. 3 in stream 352 before entry into membrane unit 390.

The resulting stream 42, 242, 342 depleted of by-products and with a regulated pressure may be fed into a first membrane separation unit 50, 250, 350 to obtain a permeate stream 54, 254, 354 rich in the dilution gas, and a retentate stream 52, 252, 352 rich in heptafluoroisobutyronitrile. This step enriches the amount of heptafluoroisobutyronitrile in the gas mixture by removing most of the dilution gas. By the term "most", it is meant that at least about 80%, at least about 85%, at least about 90%, at least about 95%, at least about 97%, at least about 98%, at least about 99% of the dilution gas is removed. In other words, the retentate stream comprises at least about 80%, at least about 85%, at least about 90%, at least about 95%, at least about 97%, at least about 98%, at least about 99% heptafluoroisobutyronitrile, in molar percentage.

The first membrane separation unit 50, 250, 350 comprises a first membrane unit feed inlet. The first membrane unit feed inlet may be downstream from a first adsorbent unit 40, 240, 340. The first membrane unit feed inlet may be connected to the first adsorbent unit 40, 240 with a conduit. The first membrane separation unit 50, 250, 350 also comprises a first permeate gas outlet and a first retentate gas outlet.

The components of the gas stream which permeate through a membrane unit faster than the heptafluoroisobutyronitrile may exit the membrane separation unit through a first permeate gas outlet. The components of the gas which are rich in heptafluoroisobutyronitrile may exit the membrane separation unit through a first retentate gas outlet. The components of the gas stream which permeate through the first membrane unit 50, 250, 350 faster than the heptafluoroisobutyronitrile exit the first membrane separation unit 50, 250, 350 through the first permeate gas outlet. The components of the gas which are rich in heptafluoroisobutyronitrile exit the first membrane separation unit 50, 250, 350 through the first retentate gas outlet. Similarly, the second membrane separation unit 260, 360 comprises a second feed inlet, a second permeate gas outlet and a second retentate gas outlet. In the case where there is a third membrane separation unit 290, 390, it may comprise a third feed inlet, a third permeate gas outlet and a third retentate gas outlet.

Membranes suitable for this unit and step are able to selectively retain heptafluoroisobutyronitrile but allow components of the dilution gas, such as $N_2$, CO and $O_2$, to pass through. In addition, the membrane should be non-reactive with the gas components.

Preferable membranes for use in this separation may be polyimides, polyamides, polyamide-imides, polyesters, polycarbonates, polysulfones, polyethersulfone, polyetherketone, alky substituted aromatic polyesters, and blends of polyethersulfone, aromatic polyimides, aromatic polyamides, polyamide-imides, fluorinated aromatic polyimide, polyamide and polyamide-imides.

The first permeate stream 54, 254, 354 may then be contacted with a second membrane in a second membrane separation unit 60, 260, 360. This step allows the separation and purification of the first permeate stream, which is rich in dilution gas. Remaining heptafluoroisobutyronitrile in the first permeate stream may be removed in this or subsequent membrane separation steps.

The heptafluoroisobutyronitrile membrane enrichment step may be repeated as many times as required to obtain an effluent stream that is enriched to a desired concentration of heptafluoroisobutyronitrile. This may occur by subjecting the retentate stream 52, 252, 352 from an initial membrane filtration step to additional membrane separation steps with additional membrane separation units.

Pressure can be controlled by adding compressor 326 to increase pressure of the gas stream if needed.

The concentration of heptafluoroisobutyronitrile in the permeate and retentate stream may be monitored by usual methods such as FTIR or GC-MS. The additional membrane separation units may be set up in series.

The retentate streams 52, 252, 352 and 62, 262, 362 from at least the first and second membrane separation units, as well as subsequent membrane separation steps and units, may be combined to form a combined retentate stream 56, 256, 356.

As in FIG. 3, the permeate streams from membrane units 350 and 360 may be combined and the subjected to a further membrane purification via membrane unit 390.

The membrane separation step may take place from about 5° C. to about 100° C. Preferably, the temperature is between about 10° C. and 80° C. More preferably, the temperature is between about 20° C. to about 25° C. to about 60° C.

The flow rate through the membrane separation unit may vary from about 0 to $10^5$ $Nm^3/h$ per $m^2$ of membrane available for separation. The flowrate may range from about $10^{-4}$ to about 10 $Nm^3/h\text{-}m^2$. The flowrate range may be from about 0.1 to about 0.5 $Nm^3/h\text{-}m^2$.

The purification of the heptafluoroisobutyronitrile and diluting gas using a first and second membrane separation unit allows the purification and recovery of the valuable heptafluoroisobutyronitrile as well as the purification of the dilution gas.

The second permeate stream 264, 364 may be subjected to contact with a metal-organic framework (MOF) material in a MOF unit 266, 366 to obtain a gas stream that is depleted of CO. MOFs are microporous solids, multidimensional structures of metallic atoms coordinated to organic ligands. The metal may be iron or nickel. They are structural materials with very high inner surface areas and ordered pore channels. If the second permeate stream 264, 364 contained $CO_2$, $O_2$ and CO, the stream exiting the MOF would only contain $CO_2$ and $O_2$, and could be released into the atmosphere. MOF unit 266, 366 may also comprise a ceria-based has catalyst for CO conversion into $CO_2$, as described in EP 3404686. The purification method of the present application therefore not only enables the purification and concentration of heptafluoroisobutyronitrile, but also enables the purification of the diluting gas so that can be released.

The retentate stream 56, 282, 382 rich in heptafluoroisobutyronitrile may then be subjected to a drying step to remove water from the stream. This may be done using a drying unit 70, 270, 370. Suitable drying unit 70, 270, 370 may be a unit comprising 3A zeolites.

The dry heptafluoroisobutyronitrile stream may then be subjected to a further filtration step to remove by-products with filter unit 80, 280, 380. The material in the filter unit 80, 280, 380 is suitable for removing decomposition by-products from the gas mixture. Suitable materials include molecular sieves, soda lime, and activated alumina. Preferably, the material is a zeolite. More preferably, the material is zeolite 5A. The temperature and flowrates of this filtration step are in the same range as that of the initial by-product filtration step.

The effluent stream exiting the final by-product trap filter is rich in heptafluoroisobutyronitrile. Preferably, the enriched stream comprises at least about at least about 80%, at least about 85%, at least about 90%, at least about 95%, at least about 98%, at least about 99%, at least about 99.5% heptafluoroisobutyronitrile.

All features of each aspects of the invention as described above can be applied to other aspects of the invention mutatis mutandis.

The invention claimed is:

1. An apparatus for purifying heptafluoroisobutyronitrile and a dilution gas from a used gas mixture comprising heptafluoroisobutyronitrile, a dilution gas and arcing by-products, the apparatus comprising at least one adsorbent unit configured to remove a first group of arcing by-products from the used gas mixture, yielding a stream depleted from by-products;

a first membrane separation unit configured to separate the used gas mixture depleted from arcing by-products into a first permeate stream and a first retentate stream, wherein the first membrane separation unit comprises a first membrane unit feed inlet, a first membrane unit permeate gas outlet and a first membrane unit retentate gas outlet, wherein the first membrane unit feed inlet is downstream from the at least one adsorbent unit;

a second membrane separation unit configured to separate the first permeate stream into a dilution gas mixture and by-products, wherein the second membrane separation unit comprises a second membrane unit feed inlet, a second membrane unit permeate gas outlet and a second membrane unit retentate gas outlet, wherein the second membrane unit feed inlet is downstream from the first membrane unit permeate gas outlet; and a metal organic framework material unit downstream of the first membrane separation unit.

2. The apparatus of claim 1, further comprising a compressor unit disposed upstream from first membrane separation unit for compressing the gas stream depleted of by-products.

3. The apparatus of claim 1, wherein the first and/or second membrane separation unit comprises a membrane selected from the group consisting of polyimides, polyamides, polyamide-imides, polyesters, polycarbonates, polysulfones, polyethersulfone, polyetherketone, alky substituted aromatic polyesters, and blends of polyethersulfone, aromatic polyimides, aromatic polyamides, polyamide-imides, fluorinated aromatic polyimide, polyamide and polyamide-imides.

4. The apparatus of claim 1, further comprising at least one adsorbent unit downstream from the second membrane separation unit.

5. The apparatus of claim 4, wherein the adsorbent unit absorbent is selected from the group consisting of molecular sieves, soda lime, and activated alumina.

6. The apparatus of claim 1, wherein the apparatus further comprises a metal-organic framework material unit downstream from the first membrane separation unit.

7. A method of purifying heptafluoroisobutyronitrile and a dilution gas from a used gas mixture comprising heptafluoroisobutyronitrile, a dilution gas and arcing by-products, the method comprising:
contacting the used gas mixture with at least one adsorbent material to generate a gas stream depleted in arcing by-products;
contacting the gas stream depleted in by-products with a first membrane and a metal organic framework material unit downstream of the first membrane separation unit to obtain a first permeate stream rich in the dilution gas, and a first retentate stream rich in heptafluoroisobutyronitrile;
contacting the first permeate stream rich in the dilution gas with a second membrane to obtain a second permeate stream rich in the dilution gas and a second retentate stream rich in heptafluoroisobutyronitrile; and
combining the first and second retentate streams rich in heptafluoroisobutyronitrile.

8. The method of claim 7, wherein the method further comprises contacting the used gas mixture with a particle filter to remove particulate matter.

9. The method of claim 7, wherein the method further comprises contacting the combined retentate streams rich in heptafluoroisobutyronitrile with a humidity filter.

10. The method of claim 7, wherein the method further comprises contacting a dehumidified stream rich in heptafluoroisobutyronitrile with an adsorbent material.

11. The method of claim 7, wherein the dilution gas comprises $CO_2$ and $O_2$.

12. The method of claim 7, wherein the method further comprises contacting the second permeate stream rich in the dilution gas with a metal-organic framework material to obtain a gas stream depleted in CO.

13. The method of claim 7, wherein the first and/or second membrane is selected from the group consisting of polyimides, polyamides, polyamide-imides, polyesters, polycarbonates, polysulfones, polyethersulfone, polyetherketone, alky substituted aromatic polyesters, and blends of polyethersulfone, aromatic polyimides, aromatic polyamides, polyamide-imides, fluorinated aromatic polyimide, polyamide and polyamide-imides.

* * * * *